(12) United States Patent
Yoshii et al.

(10) Patent No.: US 6,440,978 B2
(45) Date of Patent: Aug. 27, 2002

(54) THERAPEUTIC AGENT FOR DERMATITIS

(75) Inventors: Haruo Yoshii; Akihiro Fujita, both of Hyogo (JP)

(73) Assignee: Nippon Zoki Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/833,274

(22) Filed: Apr. 12, 2001

(30) Foreign Application Priority Data

Apr. 13, 2000 (JP) ........................................ 2000-111809

(51) Int. Cl.$^7$ ............................................ A61K 31/505
(52) U.S. Cl. ...................... 514/258; 514/858; 514/859; 514/860; 514/861; 514/862; 514/863; 514/864
(58) Field of Search ........................... 514/258, 858–864

(56) References Cited

U.S. PATENT DOCUMENTS

| | | |
|---|---|---|
| 3,235,554 A | 2/1966 | Papesch et al. |
| 3,272,816 A | 9/1966 | Papesch |
| 3,275,634 A | 9/1966 | Papesch |
| 4,808,587 A | 2/1989 | Go et al. |
| 5,264,437 A | 11/1993 | Wilhelm et al. |
| 5,338,850 A | 8/1994 | Nakamura et al. |
| 5,686,251 A | 11/1997 | Horiuchi et al. |
| 5,776,942 A | 7/1998 | Furukawa et al. |
| 6,242,452 B1 | 6/2001 | Ogino et al. |

FOREIGN PATENT DOCUMENTS

| | | |
|---|---|---|
| DE | 2317230 | 10/1973 |
| DE | 2334266 | 1/1974 |
| EP | 0 163 599 A2 | 12/1985 |
| EP | 0 260 817 A1 | 3/1988 |
| EP | 0 243 311 B1 | 6/1993 |
| EP | 0 696 590 A1 | 2/1996 |
| EP | 0 994 113 A3 | 5/2000 |
| GB | 989048 | 4/1965 |
| JP | 63-45279 | 2/1988 |
| JP | 7/504676 | 5/1995 |
| WO | WO 92/08719 | 5/1992 |
| WO | WO 93/19068 | 9/1993 |

OTHER PUBLICATIONS

Kaneko et al., "Elevated Intracellular Cyclic Amp Inhibits Chemotaxis in Human Eosinophils," *Cellular Signalling*, vol. 7, No. 5, pp. 527–534, 1995.

Alvarez et al., "Activation and Selective Inhibition of a Cyclic AMP–Specific Phosphodiesterase, PDE–4D3" *Molecular Pharmacology*, 48:616–622 (1995).

Lowe, III, et al., "Structure–Activity Relationship of Quinazolinedione Inhibitors of Calcium–Independent Phosphodiesterase" *J. Med. Chem.* 1991, 34, 624–628.

Verghese et al., "Differential Regulation of Human Monocyte–Derived TNF α and IL–1β Type IV cAMP–Phosphodiesterase (cAMP–PDE) Inhibitors" *The Journal of Pharmacology and Experimental Therapeutics*, vol. 272, No. 3, pps. 1313–1320, 1995.

Chemical Abstracts, vol. 102, No. 15, Apr. 15, 1985, pp. 625–626, abstract No. 131985x; Abstract of T .L. SU, et al., "Pyrimidines, 21, Novel reactions of 5–cyano–1,3–dimethyluracil with carbon nucleophiles. A facile preparation of certain pyrido(2,3–d)pyrimidines".

Su, et al., "Pyrimidines, 21. Novel reactions of 5–cyano–1, 3–dimethyluracil with carbon nucleophiles. A facile preparation of certain pyrido[2,3–d]pyrimidines (1)", J. Heterocycl. Chem. 1984, 21, pp. 1543–1547.

Chemical Abstracts, vol. 93, No. 9, Sep. 1, 1980, pp. 643–644, abstract No. 95234m; S. Brunel, et al.: "Synthesis of new 1H,3H–pyrido(2,3–d)pyrimidine–2,4–diones".

Chemical Abstracts, vol. 100, No. 9, Feb. 27, 1984, p. 596, abstract No. 68254z, Abstract of T. Itoh, et al.: "A simple synthesis of 1,3–dialkylpyrido(2,3–d)pyrimidines".

T. Itoh, et al.: "A simple synthesis of 1,3–dialkylpyrido(2, 3–d)pyrimidines", Chemical and Pharmaceutical Bulletin, vol. 33, No. 4, 1985, pp. 1375–1379.

(List continued on next page.)

Primary Examiner—William R. A. Jarvis
Assistant Examiner—Vickie Kim
(74) Attorney, Agent, or Firm—Hollander Law Firm, P.L.C.

(57) ABSTRACT

The present invention provides a therapeutic agent for dermatitis, particularly a therapeutic agent for atopic dermatitis, which is very safe and which shows few adverse side-effects in comparison to, for example, steroidal agents. The present invention relates to a therapeutic agent containing a compound represented by the following formula (I) or a pharmaceutically acceptable salt or hydrate thereof as an effective ingredient:

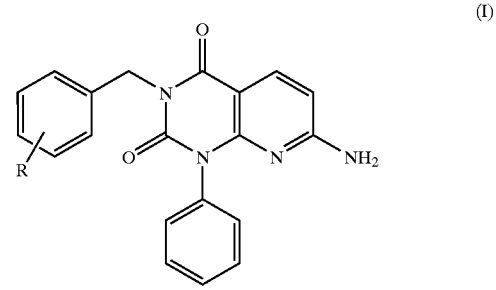

(I)

wherein R is hydrogen or a halogen. The therapeutic agent for dermatitis according to the present invention effectively and in a dose-dependent manner suppresses antigen-induced swelling in a mouse ear, a recognized animal model for atopic dermatitis, and suppresses the antigen-induced flare-up reaction in mice which occurred with the swelling reaction. In addition, no adverse reaction in the skin are observed.

11 Claims, No Drawings

OTHER PUBLICATIONS

Goto, et al., "Anti–anaphylactic activities of a new benzopyranopyridine derivative Y–12,141 in rats and guinea pigs", Japan, J. Pharmacol. 30, 1980, pp. 537–547.

Muller T., et al., "Subtypes of the type 4 cAMP phosphodiesterases: structure, regulation and selective inhibition," *Trends in Pharmacological Science, GB, Elsevier Trends Journal*, Cambridge, vol. 17, No. 8, Aug. 1, 1996, pps. 294–298, XP004034578.

Tominaga, et al., Chemical Abstracts, vol. 100, No. 209737y (1984), pps. 589–590.

Matyus, et al., Chemical Abstracts, vol. 102, No. 6405g (1985).

Rodgers, et al., Chemical Abstracts, vol. 106, No. 156415g (1987).

Rodgers, G.R., et al., "Linear expanded xanthines", Monatshefte fur Chemie (Chemical Monthly), vol. 117, 1986, pp. 879–882.

McLean, et al., *J. Chem. Soc.*, pp. 2582–2585 (1949).

Cherdantseva, N.M., et al., "Synthesis of pyrido[2,3–d] pyrimidines on the basis of 5–formyl–6–aminouracils", Chem. Heterocycl. Compounds, vol. 19, No. 6, 1983, pp. 674–677.

Burova, O.A., et al., "Pyrido[2,3–d]pyrimidines. 7. Reactions of 1,3–dimethyl–5,7–dichloro–6–nitropyrido[2,3]pyrimidine–2,4–dione with amines. Synthesis of derivatives of triazolo(4',5':4,5)pyrido[2,3–d]pyrimidine", Chem. Heterocycl. Compounds, vol. 29, No. 3, 1993, pp. 335–338.

Heber, D., et al., "Synthesis and positive inotropic activity of several 5–aminopyrido[2,3–d]pyrimidines", Die Pharmazie, vol. 48, No. 7, Jul. 1993, pp. 509–513.

Heber, D., et al., "Positivie inotropic activity of 5–amino–6–cyano–1,3–dimethyl–1,2,3,4–tetrahydropyrido [2,3–d]pyrimidine–2,4–dione in cardiac muscle from guinea–pig and man", Die Pharmazie, vol. 48, No. 7, Jul. 1993, pp. 537–541.

THERAPEUTIC AGENT FOR DERMATITIS

FIELD OF THE INVENTION

The present invention relates to medical uses of 7-amino-3-benzyl-1-phenylpyrido[2,3-d]pyrimidin-2,4-dione derivatives as a therapeutic agent for dermatitis, particularly as a therapeutic agent for atopic dermatitis.

BACKGROUND OF THE INVENTION

Dermatitis, which usually has the same meaning as eczema, is an inflammation reaction of the skin to various external and internal causes and is the most common disease among the skin diseases. Typical clinical features in acute stage dermatitis include swelling erythema, followed by the formation of papules and serous papules on the erythema. After the formation of vesicles in the skin, pustules form, followed by the erosion, crusting and desquamation of the skin. Only then does the skin begin to heal. When dermatitis turns chronic, thickening, lichenification and pigmentation of the skin all result and, in most cases, accompanied by itching. Histologically, dermatitis is characterized in swelling among epidermal cells (in a spongy state) during the acute stage. Contact dermatitis, atopic dermatitis, seborrheic dermatitis, nummular eczema, Vidal's lichen, stasis dermatitis, dyshidrotic eczema, asteatosis eczema dermatitis, autosensitization eczema, etc. are included among recognized categories of dermatitis.

Although atopic dermatitis is thought to occur by atopy, i.e. by an allergic reaction in which immunoglobulin E (IgE) participates, a definite cause of its onset is still unknown. Atopic dermatitis is often accompanied by a high level of IgE in the blood and by eosinophilia.

Atopy itself belongs to a type I allergic response but, since atopic dermatitis is a reaction similar to eczema and contact dermatitis from a pathological viewpoint, the participation of a type IV allergic response (delayed type) has been suggested. It has also been suggested that a delayed type reaction accompanied by infiltration of eosinophils and lymphocytes plays an important role in the onset of atopic dermatitis and its change to chronic dermatitis. See Iwamoto, et al.: J. Leukoc. Biol., 52, pages 572–578 (1992); Frigas, et al.: *J. Allergy Clin. Immunol.*, 77, pages 527–537 (1986), etc.

Symptoms of atopic dermatitis vary with age of the subject. At from about the second to the sixth month from birth, weeping eczema of the face appears first and then it gradually expands to the legs and arms and to the trunk. A strong itch is also characteristic. The symptoms are classified into a baby period (younger than 2 years old), an infant period (2–12 years old) and an adult period. During the baby period, the onset is mostly limited to the face but, gradually the skin of trunk becomes dry resulting in follicular papules (atopic skin). In infants and small children, the lesions become dry and thick areas form in the pits of the elbow and knee (lichenification). There are many cases where atopic dermatitis heals by about 12 years of age but when it carries over into an adult period, it becomes more severe. Even if the atopic dermatitis once attenuates in severity, recurrence and the worsening of symptoms are often seen and there are even some cases which require a long period to complete healing or else a complete healing is not achieved.

External application of a steroidal agent (ointment or the like) is the most effective therapy to date and no therapeutic method to replace it has yet been established. However, steroid preparations which are frequently used to treat dermatitis, including atopic dermatitis, are the pharmaceuticals which have a very active clinical effect and which also cause a great variety of adverse reactions. There have been various reports on the side effects of steroid preparations and, in the case of agents for external use such as ointments, direct harmful effects such as the thinning, shrinking and flushing of the skin have become a widespread social problem. The severe adverse reactions caused by steroid preparations used as remedies for dermatitis and atopic dermatitis have led to an eager demand in patients and in the medical field for safer pharmaceuticals which have fewer side effects.

The compounds which are used as a therapeutic agent for dermatitis according to the present invention are disclosed in Japanese Patent Laid-Open Publication 2000-119272 and in corresponding U.S. patent application Ser. No. 09/418982 to Ogino et al. Compounds having a pyrido[2,3-a]pyrimidine structure, have been reported as having an anti-allergic action. See Japanese Patent Laid-Open Publication Sho-63/45279 and U.S. Pat. No. 4,808,587 to Go et al. Further, compounds having a 7-aminopyrido[2,3-d]pyrimidine structure have a bronchodilating action. See Japanese Patent Publications 06-159322, 06-159323, and 06-159324 (Hei-8/3046, Hei-8/3164 and Hei-8/3165) and corresponding U.S. Pat. No. 5,776,942 to Furukawa et al.

None of the references discussed above disclose a medical use or a method for treating dermatitis or atopic dermatitis using a compound made according to the present invention. The present invention solves the above-mentioned problems by providing a therapeutic agent for dermatitis, particularly a therapeutic agent for atopic dermatitis, which is safer and which exhibits fewer adverse side-effects than existing therapeutic agents for dermatitis or atopic dermatitis.

SUMMARY OF THE INVENTION

The present inventors have carried out an intensive investigation of 7-aminopyrido[2,3-d]pyrimidine derivatives and have found that 7-amino-3-benzyl-1-phenylpyrido [2,3-d] pyrimidin-2,4-dione derivatives are highly effective as therapeutic agents for dermatitis, particularly for atopic dermatitis, and that these therapeutic agents for dermatitis cause few adverse reactions in the skin.

The present invention provides a therapeutic agent for dermatitis which contains a compound represented by the following formula (I), or a pharmaceutically acceptable salt or hydrate thereof, as an effective ingredient:

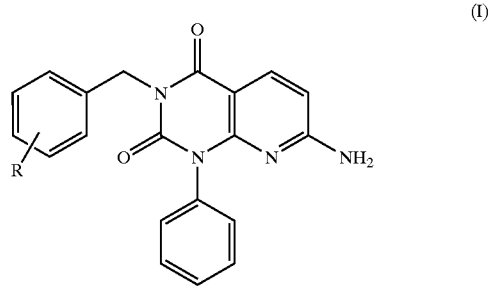

(I)

In the formula, R is hydrogen or a halogen.

Compounds represented by the above formula (I) include the pharmaceutically acceptable salts thereof such as acid addition salts, salts with alkali metals, salts with alkaline-earth metals, salts with other metals or salts with bases.

The present invention includes any and all steric isomers such as cis-trans isomers, optical isomers, conformational isomers and hydrates of the compounds of formula (I).

A pharmaceutical composition which is used as a therapeutic agent for dermatitis according to the present invention can be prepared by combining a compound represented by the above formula (I) with a pharmaceutically acceptable carrier or diluent.

DETAILED DESCRIPTION OF THE INVENTION

The present invention provides a therapeutic agent and a method of using a therapeutic agent which comprises 7-amino-3-benzyl-1-phenylpyrido [2,3-d]pyrimidin-2,4-dione derivatives for treating dermatitis, and particularly for atopic dermatitis. Specifically, the present invention provides a therapeutic agent for dermatitis which contains a compound represented by the following formula (I), or a pharmaceutically acceptable salt or hydrate thereof, as an effective ingredient:

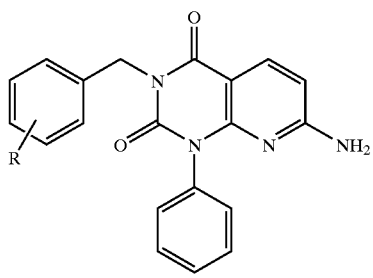

In the formula, R is hydrogen or a halogen. A "halogen" includes, but is not limited to, fluorine, chlorine, bromine or iodine.

Preferred embodiments of the present invention are (1) A therapeutic agent for dermatitis containing a compound represented by the above formula (I) or a pharmaceutically acceptable salt or hydrate thereof as an effective ingredient.

(2) The therapeutic agent for dermatitis according to paragraph (1), wherein the agent is a therapeutic agent for atopic dermatitis.

(3) The therapeutic agent for dermatitis according to paragraphs (1) or (2), wherein the agent is for external use.

(4) The therapeutic agent for dermatitis according to any of paragraphs (1) to (3), wherein R is hydrogen in formula (I).

(5) The therapeutic agent for dermatitis according to any of paragraphs (1) to (3), wherein R is substituted at the o-position in formula (I).

(6) The therapeutic agent for dermatitis according to paragraph (5), wherein R is chloride.

Especially preferred compounds for use in treating dermatitis are:

7-amino-3-benzyl-1,2,3,4-tetrahydro-1-phenylpyrido[2,3-d]pyrimidin-2,4-dione (compound 1)

7-amino-3-(2-chlorobenzyl)-1,2,3,4-tetrahydro-1-phenylpyrido[2,3-d]pyrimidin-2,4-dione (compound 2)

The most preferred compound is the compound 1.

Compounds represented by the above formula (I) include the pharmaceutically acceptable salts thereof such as acid addition salts with hydrochloric acid, sulfuric acid, nitric acid, hydrobromic acid, phosphoric acid, perchloric acid, thiocyanic acid, boric acid, formic acid, acetic acid, haloacetic acid, propionic acid, glycolic acid, citric acid, tartaric acid, succinic acid, gluconic acid, lactic acid, malonic acid, fumaric acid, anthranilic acid, benzoic acid, cinnamic acid, p-toluenesulfonic acid, naphthalenesulfonic acid or sulfanilic acid; salts with alkali metal such as sodium or potassium, salts with an alkaline-earth metal such as calcium or magnesium, or salts with other metals such as aluminum; or salts with bases such as ammonia or organic amines. Those salts may be manufactured by known methods from the compounds of the present invention in a free state or may be mutually converted among the salts. The present invention includes any and all steric isomers such as cis-trans isomers, optical isomers, conformational isomers and hydrates of the compounds of formula (I).

A pharmaceutical composition which is used as a therapeutic agent for dermatitis according to the present invention can be prepared by combining a pharmaceutically effective amount of a compound represented by the above formula (I) with an appropriate pharmaceutically acceptable carrier or diluent. In manufacturing the pharmaceutical composition, any of various conventional methods may be used. Optimally, a therapeutic agent for dermatitis comprises a preparation for external use such as a liquid, suspension/emulsion, plaster, ointment, cataplasm, liniment or lotion. For prescription, the compound of the above formula (I) may be used as a pharmaceutically acceptable salt or hydrate, or it may be combined with other pharmaceutically active ingredient(s). Methods for the manufacture of preparations for external use are mentioned in detail, for example, in General Rule for Pharmaceutical Preparations, Commentary to the 13th Revision of the Japanese Pharmacopoeia (published by Hirokawa Shoten, 1996), the disclosure of which is herein incorporated by reference in its entirety.

Ointment preparations may be roughly classified into fat/oil type ointments, emulsified ointments, water-soluble ointments and suspended ointments according to the type of the base (vehicle) used therefor. An ointment may comprise, for example, fats, fatty oils, lanolin, vaseline, paraffins, waxes, resins, plastics, glycols, higher alcohols, glycerol, water, emulsifiers, suspending agents or other appropriate additives as a diluent, carrier or as a vehicle. Manufacture of an ointment comprises, for example, adding the compound of the present invention to the appropriate additives, diluents, carriers or vehicles followed by mixing to make the mixture homogeneous.

In manufacturing a cataplasm, a powder of the compound of the above formula (I) may be admixed with an essential oil component to give a muddy product. Depending upon the type and state of the disease to be treated, the ordinary skilled artisan can manufacture other types of preparations which are optimum for the desired therapy.

A therapeutic agent according to the present invention, or a pharmaceutical composition which is used as a therapeutic agent for dermatitis according to the present invention may be used to treat animal or human subjects who have been diagnosed with or who are known to be in need of treatment for dermatitis or eczema, such as one or more conditions selected from the group consisting of contact dermatitis, atopic dermatitis, seborrheic dermatitis, nummular eczema, Vidal's lichen, stasis dermatitis, dyshidrotic eczema, asteatosis eczema dermatitis, and autosensitization eczema.

The preferred dosage of the compound of the present invention varies depending upon the subject to be administered (age, body weight, symptoms, etc. of the patient), form of the preparation, method for the administration, term for the administration, etc. For example, to achieve the desired effect, the compound of the present invention may be administered as an ointment containing, by weight based on the total weight of the ointment, from about 0.1% to about 15% of the compound of the present invention. The ointment may be applied on the affected area once to several times per day, for example, 5 or 6 times daily until the affected area heals.

Compounds represented by the above formula (I) can be manufactured by methods disclosed in: a) Japanese Patent Laid-Open Sho-63/45279, corresponding U.S. Pat. No. 4,808,587 to Go et al. and corresponding publication EP 0243311 B; b) Japanese Patent publications 06-159322, 06-159323 and 06-159324 (Hei-8/3049, Hei-8/3164, Hei-8/3165), corresponding U.S. Pat. No. 5776942 to Furukawa et al., and corresponding European patent publication EP 0696590 A; and c) Japanese Patent Laid-Open Publication 2000-119272, corresponding U.S. patent application Ser. No. 09/418982 to Ogino et al., and corresponding European patent publication EP 0994113 A or by a similar method. The disclosure of each of said Japanese and European patent publications, U.S. Pat. Nos 4,808,587 and 5,776,942, and U.S. application Ser. No. 09/418,982 to Ogino et al are each herein incorporated by reference in their entireties.

Methods for the production of the compounds of the present invention are further illustrated in detail by way of the following non limiting examples. The starting materials may be purchased from Aldrich Chemical Co., Inc.; Furuka Chemical Inc.; Lancaster Synthesis Inc.; Maybridge Chemical Co., Ltd.; or Tokyo Kasei K.K. or may be synthesized by known methods mentioned in the literature such as *J. Org. Chem.*, 16, 1879 (1951); *J. Am. Chem. Soc.*, 75,114 (1953); etc. In the following examples all parts, percentages and ratios are by weight, all temperatures are in ° C., and all reactions are conducted at about atmospheric pressure and at about room temperature unless indicated to the contrary:

EXAMPLE 1

Preparation of Ointment (1) Manufacture of 6-Amino-1-phenyluracil

Phenylurea (68.1 g, 0.5 mol) and ethyl cyanoacetate (53 mL, 0.5 mol) were added to a solution prepared by mixing methanol (400 mL) with potassium tert-butoxide (67.3 g, 0.6 mol). The mixture was heated under reflux for 5.5 hours and the solvent was evaporated in vacuo until a residue was formed. The residue was then dissolved in hot water (2 L). Glacial acetic acid was added to the solution until the solution became acidic and a uracil derivative was obtained as a bulky and yellowish precipitate. The precipitate was collected by filtration, washed several times with water and dried at 50° C. to give 6-amino-1-phenyluracil (67.4 g) in a 66% yield.

Mp:>280° C.; $^1$H-NMR (DMSO-$d_6$)δ: 4.67(s,1H), 6.08 (s,2H), 7.31(d,2H,J=7Hz), 7.47–7.54(m,3H), 10.43(s,1H); IR (KBr): 3478, 3334, 2981, 1712, 1634, 1476, 1387, 1299, 704 cm$^{-1}$; MS (El) m/z: 203[M$^+$], 160, 132, 77.

(2) Manufacture of 7-Amino-1,2,3,4-tetrahydro-1-phenylpyrido [2,3-d]pyrimidin-2,4-dione 6-Amino-1-phenyluracil (30.5 g, 150 mmol) and propene 3-methoxycyanide (25 mL, 225 mmol) were added to a solution prepared by mixing tert-butanol (300 mL) with potassium tert-butoxide (18.7 g, 225 mmol). The mixture was heated at 110° C. for 12 hours with stirring until the butanol was evaporated. Water (200 mL) was then added to the evaporation residue and the resulting mixture was acidified with acetic acid. The precipitate was collected by filtration and washed with hot ethanol to give 7-amino-1,2,3,4-tetrahydro-1-phenylpyrido [2,3-d]pyrimidin-2,4-dione (20 g) in a 53% yield.

Mp:>300° C.; $^1$H-NMR (DMSO-$d_6$)δ: 6.27(d,1H,J=9Hz), 6.89(s,2H), 7.20–7.87(m,5H),; 7.88(d,1H,J=9 Hz), 11.26(s, 1H); IR (KBr): 3038, 1709, 1605, 1417, 789 cm$^{-1}$; MS (El) m/z: 254[M$^+$], 211, 77.

(3) Manufacture of 7-amino-1,2,3,4-tetrahydro-1-phenylpyrido[2,3-d]pyrimidin-2,4-dione (compound 1)

A suspension prepared by adding 7-amino-3-benzyl-1,2, 3,4-tetrahydro-1-phenylpyrido[2,3-d]pyrimidin-2,4-dione (3 g, 12 mmol) and ammonium sulfate (500 mg) to hexamethyldisilazane (100 mL) was refluxed at room temperature and atmospheric pressure for 24 hours. The solvent was evaporated and the residue was dissolved in 100 mL of L(-)-5,6,7,8-tetrahydrofolic acid (THF). Into this solution was dropped a solution prepared by adding benzyl bromide (2 mL, 18 mmol) and 1 M Bu4NF to THF (14 mL, 14 mmol) under reflux. The mixed solution was stirred for 2 hours and concentrated in vacuo. The residue was purified by silica gel column chromatography (benzene:acetone=5:1) and recrystallized from methanol to give 7-amino-3-benzyl-1,2,3,4-tetrahydro-1-phenylpyrido[2,3-d]pyrimidin-2,4-dione [compound 1] (1 g) in a 27% yield.

Mp: 261–262° C.; $^1$H-NMR (DMSO-$d_6$)δ: 5.08(s,2H), 6.32(d,1H,J=8 Hz), 6.98(s,2H), 7.22–7.49(m,10H), 7.94(d, 1H,J=8Hz); IR (KBr): 3498, 3392, 1695, 1655, 1618, 787, 700 cm$^{-1}$; Anal. Calcd for $C_{20}H_{16}N_4O_2$: C, 69.76; H, 4.68; N, 16.27; Found: C, 69.81; H, 4.77; N, 16.13; MS (El) m/z: 344[M$^+$], 211,91.

7-amino-3-(2-chlorobenzyl)-1,2,3,4-tetrahydro-1-phenylpyrido[2,3-d]pyrimidin-2,4-dione (compound 2) may also be prepared by utilizing the above methods of subparagraphs (1) to (3), for example by employing 2-chlorobenzylbromide as a reactant instead of benzylbromide.

(4) Preparation of an Ointment

The compound 1 or 2, prepared as above, was thoroughly suspended in white vaseline in a mortar to prepare an ointment having a final concentration, by weight, of about 0.3%, about 1%, about 3% or about 10% of compound 1 or 2. As a control, an ointment consisting only of a base was prepared. As a positive control, an ointment containing 0.12% of betamethasone valerate (a steroid preparation) was prepared.

EXAMPLE 2

Preparation of Animal Model for Atopic Dermatitis

Seven week old BALB/c female (SPF) mice of were selected as subjects. According to a method of Tanaka, et al. (*Allergy*, 46, pages 42–48(1997)), egg white albumin (final concentration: 2 μg/mL) and aluminum hydroxide gel (final concentration: 10 mg/mL) were suspended in physiological saline and 0.5 mL of the suspension was administered to effect intraperitoneal sensitization on the first day of the test. On the 14th day of the test, an additional sensitization was carried out under the same conditions. Further, on the 28th day of the test, 25 μL of egg albumin (a 20 μg/mL solution in physiological saline) was intradermally administered to the right ear of a mouse to induce a swelling reaction.

This swelling reaction reached its peak at 4 hours after the challenge by the antigen. Even after 24 to 48 hours, a significant swelling reaction was noted as compared with the control in which antigen was merely challenged (not sensitized). In this model, the reaction at 1–4 hour(s) after the challenge is thought to be a swelling reaction of an immediate type caused by various mediators from mast cells and it seems that inflammation cells, such as eosinophils and lymphocytes, do not participate in the reaction. On the contrary, the swelling from 24 to 48 hours after the challenge is thought to be the so-called delayed-type swelling reaction accompanied by infiltration of eosinophils, neutrophils and lymphocytes. In addition, a flare-up reaction having a peak at 24 hours after the challenge appeared on the ear of the antigen-induced site. Like swelling, flare-up is an important symptom of inflammation. Although the mechanism of the flare-up reaction is ambiguous, it may be a flare-up reaction of a delayed type in view of the time course of its expression. As such, this model animal in which the inflammation of both immediate and delayed types are induced is appropriate as a model animal for atopic dermatitis. In the following experiment, the effectiveness of the therapeutic agent for dermatitis according to the present invention was tested using the said model animal.

The following Examples 3 to 6 show the results of an investigation of the effectiveness and safety of the therapeutic agent for dermatitis according to the present invention. In the following Examples, the result is given by a mean value ± standard deviation and a statistical library (Yukms) was used to evaluate the statistical accuracy of the differences observed between the subject groups. A Student's two-sided unpaired t-test was used to analyze the differences between the vehicle-only control group and the challenge-only group or the untreated group, while Dunnett's two-sided multiple comparison test or the Mann-Whitney test was used to analyze the differences between the control group and the test drug group.

In Examples 3 to 6 below, the letter "n" refers to the number of mice or other animals tested in each subject group. A "challenge" is defined as an exposure of a subject to the antigen which causes dermatitis. Such a challenge usually does not result in a swelling reaction or dermatitis unless the challenge follows an initial sensitization, usually an intradermal exposure, of a subject to the antigen which causes dermatitis.

deducting the thickness (early value) measured before the challenge from the thickness of the swelling induced ear. The suppression rate of the test drug for ear swelling was calculated by the following formula:

Suppression Rate (%)=100 ×[(Ear Thickness Increase of Vehicle-Only-Control)−(Ear Thickness Increase of the Test Group)]/[(Ear Thickness Increase of the Vehicle-Only-Control)−(Ear Thickness Increase of the Challenge-Only-Group)]

Test results are shown in Tables 1 and 2. The therapeutic agent for dermatitis according to the present invention significantly and dose-dependently suppressed the antigen-induced swelling reaction in a mouse ear.

TABLE 1

| | n | Ear Thickness Increase at 1 hr after Challenge × 0.01 mm (Suppression Rate) | Ear Thickness Increase at 4 hr after Challenge × 0.01 mm (Suppression Rate) | Ear Thickness Increase at 8 hr after Challenge × 0.01 mm (Suppression Rate) | Ear Thickness Increase at 24 hr after Challenge × 0.01 mm (Suppression Rate) | Ear Thickness Increase at 48 hr after Challenge × 0.01 mm (Suppression Rate) |
|---|---|---|---|---|---|---|
| Challenge Only | 2 | 6.5 ± 0.5# | 4.0 ± 1.0### | 3.5 ± 1.5### | 2.0 × 2.0### | 2.0 ± 2.0### |
| No-Treatment-Control | 5 | 9.0 ± 1.1 | 25.2 ± 0.9 | 19.2 ± 0.6 | 14.0 ± 1.5 | 9.2 ± 1.6 |
| Vehicle-Only-Control | 5 | 9.8 ± 0.6 | 25.2 ± 0.6 | 20.4 ± 1.1 | 17.0 ± 1.0 | 11.2 ± 0.9 |
| Positive Control (Steroid Preparation, 0.12% Ointment) | 3 | 8.3 ± 0.7 (45.5%) | 16.3 ± 2.0** (42.0%) | 2.0 ± 1.2** (49.7%) | 5.0 ± 1.0** (80.0%) | 2.0 ± 1.0** (100.0%) |
| Compound 1 (1% Ointment) | 4 | 6.3 ± 1.4* (106.1%) | 18.0 ± 0.9** (34.0%) | 16.0 ± 0.4* (26.0%) | 9.3 ± 1.1** (51.3%) | 6.8 ± 1.0 (47.8%) |
| Compound 1 (3% Ointment) | 4 | 5.3 ± 0.5** (136.4%) | 2.3 ± 0.9* (18.4%) | 15.8 ± 1.4* (27.2%) | 7.8 ± 0.9** (61.3%) | 5.3 ± 0.9* (64.1%) |

Average ± Standard Error
Significant Difference from Base-Only-Control:
*P < 0.05,
**P < 0.01 (Dunnett Multiple Comparison)
P < 0.05,
P < 0.001 (Student's t-Test)

EXAMPLE 3

Suppressive Action Against an Antigen-Induced Swelling Reaction in a Mouse Ear

Each of a vehicle (control) and a test agent (containing the compound of the present invention or a positive control) was applied to the antigen-induced site (right auricle) of a mouse. A swelling reaction was induced in accordance with Example 2 at 2 hours before and 4 hours after the challenge. After the challenge, the thickness of the swelling induced ear was measured by a Dial Thickness Gauge (manufactured by Ozaki Seisakusho). The intensity of the reaction was expressed in terms of an increase in the auricle thickness by

TABLE 2

| | n | Ear Thickness Increase at 4 hr after Challenge × 0.01 mm (Suppression Rate) | Ear Thickess Increase at 24 hr after Challenge × 0.01 mm (Suppression Rate) |
|---|---|---|---|
| Challenge Only | 1 | 2.0 | 1.0 |
| Vehicle-Only-Control | 4 | 24.5 ± 1.7 | 16.5 ± 1.6 |
| Positive Control (Steroid Preparation, 0.12% Ointment) | 4 | 11.0 ± 0.6** (60.0%) | 6.3 ± 2.4* (65.8%) |
| Compound 1 (3% Ointment) | 4 | 13.3 ± 0.3** (49.8%) | 9.3 ± 1.7 (46.5%) |
| Compound 1 (0.3% Ointment) | 4 | 20.3 ± 2.4 (18.7%) | 13.5 ± 1.3 (19.4%) |
| Compound 2 (1% Ointment) | 4 | 19.5 ± 3.2 (22.2%) | 11.8 ± 2.6 (30.3%) |
| Compound 2 (3% Ointment) | 4 | 19.3 ± 2.4 (23.1%) | 8.0 ± 1.4* (54.8%) |

Average ± Standard Error
Significant Difference from Base-Only-Control:
*P < 0.05,
**P < 0.01 (Dunnett Multiple Comparison)

EXAMPLE 4

Suppressive Action Against an Antigen-Induced Flare-Up Reaction in a Mouse

Each of a vehicle (control) and an agent for the test (the therapeutic agent for dermatitis according to the present invention or a positive control) was applied to the antigen-induced site (right auricle) of a mouse to induce a swelling reaction in accordance with Example 2 at 2 hours before and 4 hours after the challenge. The right ear was observed by naked eye and the degree of flare-up was scored according to the following standard:

0: no flare-up
1: in such a degree that a flare-up was confirmed, the color is clear red or pale red and the size was small
2: between score 3 and score 1
3: color of the flare-up was clearly red and the size of the flare-up was big An example of the result is shown in Table 3. The therapeutic agent for dermatitis according to the present invention significantly suppressed the antigen-induced flare-up reaction in mice.

TABLE 3

|  | n | Flare-up Score at 4 hr after Challenge (Suppression Rate) | Flare-up Score at 24 hr after Challenge (Suppression Rate) |
|---|---|---|---|
| Vehicle-Only-Control | 23 | 0.8 ± 0 | 2.5 ± 0.2 |
| Positive Control (Steroid Preparation, 0.12% Ointment) | 20 | 0.6 ± 0 (25.0%) | 1.5 ± 0.2*** (40.0%) |
| Compound 1 (3% Ointment) | 22 | 0.8 ± 0 (0.0%) | 1.7 ± 0.2* (32.0%) |

Average ± Standard Error
Significant Difference from Base-Only-Control:
*P < 0.05,
**P < 0.001 (Mann-Whitney test)

EXAMPLE 5

Suppressive Action Against Eosinophil Infiltration Into the Antigen-Induced Ear of a Mouse The degree of eosinophil infiltration into the ear of a mouse was determined by measuring eosinophil peroxidase activity in a skin tissue homogenate and using the measurement as an index. Each of the vehicle (control) and the test drug (the therapeutic agent for dermatitis according to the present invention or a positive control) was applied to the antigen-induced site (right auricle) where a swelling reaction was induced according to Example 2 at 2 hours before and 4 hours after the challenge. 24 hours after the challenge, the right ear was cut, ear tissues were pooled in one group and a homogenate of the ear tissues was prepared according to the method of Holliday, et al. (*Toxicology*, 106, pages 237–242 (1996)). This homogenate was centrifuged at 20,000 rpm for 20 minutes (using KR-20000T, Kubota) and the peroxidase activity in the supernatant fluid was measured using o-phenylenediamine dihydrochloride (Sigma) as a substrate. By measuring the absorbance of radiation having a wavelength of 492 nm, the resulting reaction curve was substantially linear relative to the dosage of the test drug and the degree of eosinophil infiltration was compared by defining the eosinophil infiltration of the control as 100%.

The therapeutic agent for dermatitis according to the present invention suppressed eosinophil infiltration into an antigen-induced mouse ear in a dose-dependent manner. The eosinophil infiltration suppressing action of a 3% ointment of the compound 1 occurred in the same degree as that of the steroid preparation of the positive control.

EXAMPLE 6

Influence of Repeated Application on the Ear Thickness of a Normal Mouse

The therapeutic agent for dermatitis according to the present invention or the positive control (steroid preparation) was applied twice daily to the right ear of a normal mouse for a total of nine times and, 2 hours after the final application, the thickness of the ear was measured.

Test results are shown in Table 2. As shown in the above test result, the therapeutic agent for dermatitis according to the present invention showed excellent ear swelling suppressive action, flare-up suppressive action and eosinophil infiltration suppressive action in a 3% ointment. And, even with the repeated application of a 10% ointment which was considerably in a higher concentration than the above, no influence on the skin was noted at all. However, the repeated application of a positive control (steroid preparation) significantly reduced the auricle thickness.

TABLE 4

|  | n | Ear Thickness × 0.01 mm (Suppression Rate) |
|---|---|---|
| No Treatment | 6 | 22.2 ± 0.4 |
| Vehicle-Only-Control | 6 | 22.5 ± 0.2 |
| Positive Control (Steroid Preparation, 0.12% Ointment) | 6 | 18.3 ± 0.5** |
| Compound 1 (3% Ointment) | 6 | 22.3 ± 0.2 |
| Compound 1 (10% Ointment) | 6 | 22.3 ± 0.5 |

Average ± Standard Error
Significant Difference from Base-Only-Control:
**P < 0.01 (Dunnett Multiple Comparison)

EXAMPLE 7

Suppressive Action Against Chemotaxis in Guinea Pig Eosinophils in the Abdominal Cavity The suppressive effect of the compounds of the present invention on the leukotriene $B_4$ or $LTB_4$ induced chemotaxis of guinea pig eosinophils in the abdominal cavity were investigated using a modified Boyden chamber method. The guinea pig eosinophils in the abdominal cavity were prepared using Hartley male guinea pigs according to the conventional method. The chemotaxis of the eosinophils was induced by $10^{-7}$ M of leukotriene $B_4$ or $LTB_4$ in 37° C. for 2 hours in the presence or absence of the test drug (the therapeutic agent for dermatitis of the present invention). After the chemotaxis cells were fixed and stained using the Giemsa stain, the number of chemotaxis cells was counted in visual fields of a microscope (×400). The experiments were repeated several times and the suppression rate of the test drug was calculated by the following formula:

Suppression Rate (%)=100×[(the number of chemotaxis eosinophils in control group)—(the number of chemotaxis eosinophils in the test drug group)]/[(the number of chemotaxis eosinophils in control group)—(the number of spontaneous chemotaxis eosinophils)]

The 50% inhibitory concentration ($IC_{50}$) was calculated from the regression line obtained by the least square method based on the calculated suppression rates.

As a result of 5 trials, Compound 1 showed a remarkable suppressive action against eosinophil chemotaxis ($IC_{50}$ of Compound 1:1.9±0.4 μmol/L).

EXAMPLE 8

Inhibitory Action Against Phosphodiesterase

The inhibitory action of the compounds of the present invention against activities of various phosphodiesterase (PDE) isozymes were investigated using the conventional method. Each of the inhibitory action of the compounds of the present invention on the activities of phosphodiesterase type II (PDE II) partially purified from human platelets, phosphodiesterase type III (PDE II) partially purified from human platelets, phosphodiesterase type IV (PDE IV) partially purified from human U937 promonocytic leukemia cells and phosphodiesterase type V (PDE V) partially purified from human platelets were measured.

A 100 μM concentration of the present compound 1 exhibited the following suppression activities against PDE II, III, IV and V: 6%, 22%, 82% and 15%, respectively. As shown above, the results clearly indicate a PDE IV selective inhibitory effect. Furthermore, this PDE IV inhibitory effect was dose dependent.

As shown in the above animal experiment, 7-amino-3-benzyl-1-phenylpyrido[2,3-d]pyrimidin-2,4-dione derivatives according to the present invention significantly and dose-dependently suppressed the antigen-induced auricle swelling reaction in mice, which was used as an atopic dermatitis model, and also significantly suppressed the antigen-induced flare-up reaction in mice accompanied therewith. The compounds also had a suppressive action against eosinophil infiltration into the antigen-induced auricle of a mouse. Accordingly, the 7-amino-3-benzyl-1-phenylpyrido [2,3-d] pyrimidin-2,4-dione derivatives of the present invention are useful as a therapeutic agent for dermatitis such as atopic dermatitis, eczema and contact dermatitis.

Further, a direct adverse reaction in the skin, such as thinning of the skin noted in the case of steroid preparations, was not observed at all in the therapeutic agent for dermatitis according to the present invention. Said therapeutic agent was very safe.

As mentioned hereinabove, the therapeutic agent for dermatitis according to the present invention is useful as a therapeutic agent for atopic dermatitis and dermatitis, and is a very safe pharmaceutical agent causing little adverse reaction in subjects treated with said agent. Accordingly, the therapeutic agent for dermatitis according to the present invention unexpectedly solves the technical problems in the art and is highly useful as an agent for which there has been a brisk demand from patients and the medical field.

What is claimed is:

1. A method for the treatment of dermatitis comprising administering to a patient in need of such treatment a pharmaceutically effective amount of at least one compound represented by the following formula (I) or a pharmaceutically acceptable salt or hydrate thereof:

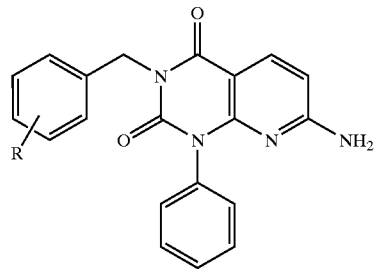

wherein R is hydrogen or halogen.

2. The method according to claim 1, wherein the dermatitis is atopic dermatitis.

3. The method according to claim 1, wherein R is hydrogen.

4. The method according to claim 1, wherein R is chloride and is substituted at the opposition.

5. The method according to claim 1 comprising applying said compound represented by formula (I) externally to an affected area of the skin.

6. The method according to claim 5 comprising applying said compound represented by formula (I) externally to an affected area of the skin from one to six times a day until the affected area heals.

7. The method according to claim 5, wherein said compound represented by formula (I) is formulated into a liquid, a suspension or emulsion, a plaster, an ointment, a cataplasm, a liniment or a lotion.

8. The method according to claim 7, wherein the formulation is an ointment.

9. The method according to claim 8, wherein the ointment contains from about 0.1% by weight to about 15% by weight based on the total weight of the ointment, of said compound represented by formula (I).

10. The method according to claim 9, wherein the ointment contains from about 0.3% by weight to about 10% by weight based on the total weight of the ointment, of said compound represented by formula (I).

11. The method according to claim 1, wherein the patient is suffering from dermatitis selected from the group consisting of contact dermatitis, atopic dermatitis, seborrheic dermatitis, nummular eczema, Vidal's lichen, stasis dermatitis, dyshidrotic eczema, asteatosis eczema dermatitis, and autosensitization eczema.

* * * * *